(12) United States Patent
Wekel et al.

(10) Patent No.: US 11,769,599 B2
(45) Date of Patent: Sep. 26, 2023

(54) EVALUATION OF DECISION TREE USING ONTOLOGY

(71) Applicant: KONINKLIJKE PHILIPS N.V., Eindhoven (NL)

(72) Inventors: Tilman Wekel, Krummesse (DE); Alexandra Groth, Hamburg (DE); Rolf Jürgen Weese, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 125 days.

(21) Appl. No.: 16/300,104

(22) PCT Filed: Jun. 27, 2017

(86) PCT No.: PCT/EP2017/065810
§ 371 (c)(1),
(2) Date: Nov. 9, 2018

(87) PCT Pub. No.: WO2018/002025
PCT Pub. Date: Jan. 4, 2018

(65) Prior Publication Data
US 2019/0139647 A1    May 9, 2019

(30) Foreign Application Priority Data
Jun. 27, 2016    (EP) .................... 16176377

(51) Int. Cl.
*G16H 70/20*    (2018.01)
*G16H 50/20*    (2018.01)
(Continued)

(52) U.S. Cl.
CPC ........... *G16H 70/20* (2018.01); *G06F 16/313* (2019.01); *G06F 16/904* (2019.01); *G16H 10/60* (2018.01); *G16H 50/20* (2018.01)

(58) Field of Classification Search
CPC ........ G16H 70/20; G16H 10/60; G16H 50/20; G06F 16/904; G06F 16/313; G06F 19/325
(Continued)

(56) References Cited

U.S. PATENT DOCUMENTS 6,334,192 B1 * 12/2001 Karpf .................... G16H 50/30
714/1
8,015,136 B1    9/2011 Baker et al.
(Continued)

FOREIGN PATENT DOCUMENTS

CN    102016859 A    4/2011
WO    2014197669 A1    12/2014

OTHER PUBLICATIONS

Peleg, M., "Computer-interpretable clinical guidelines: A methodological review", Journal of Biomedical Informatics, vol. 46, Issue 4, Aug. 2013, pp. 744-763.
(Continued)

*Primary Examiner* — Michael Tomaszewski
*Assistant Examiner* — Rachael Sojin Stone

(57) ABSTRACT

A system and method are provided for use in evaluating a clinical guideline which is represented in a machine readable version by a decision tree comprising at least one node and a decision rule associated with the node. The decision rule comprises at least one variable representing a biomedical quantity. The biomedical quantity is extracted from the patient data using an ontology which defines concepts and their relationships in a medical domain of the clinical guideline and which thereby relates the variable of the decision rule to the patient data. If said extraction is not possible, a view of the patient data is presented to the user to enable the user to determine the biomedical quantity from the view. Advantageously, the user is assisted in evaluating the clinical guideline even when it is not possible to auto-
(Continued)

matically extract the biomedical quantity from the patient data.

12 Claims, 6 Drawing Sheets

(51) Int. Cl.
  *G16H 10/60* (2018.01)
  *G06F 16/904* (2019.01)
  *G06F 16/31* (2019.01)
(58) Field of Classification Search
  USPC .............................................................. 705/3
  See application file for complete search history.

(56) References Cited

U.S. PATENT DOCUMENTS

| | | | |
|---|---|---|---|
| 11,348,691 B1* | 5/2022 | Kenedy | G06F 16/24575 |
| 2005/0170323 A1* | 8/2005 | Jarrell | G09B 23/28 |
| | | | 434/262 |
| 2007/0130206 A1 | 6/2007 | Zhou et al. | |
| 2008/0015418 A1* | 1/2008 | Jarrell | G09B 5/00 |
| | | | 600/300 |
| 2008/0201280 A1 | 8/2008 | Martin et al. | |
| 2010/0094874 A1 | 4/2010 | Huber et al. | |
| 2010/0111370 A1* | 5/2010 | Black | G06K 9/00369 |
| | | | 382/111 |
| 2010/0204973 A1* | 8/2010 | Parkinson | G16B 50/30 |
| | | | 703/11 |
| 2012/0154582 A1* | 6/2012 | Johnson | G16H 10/60 |
| | | | 348/143 |
| 2012/0310947 A1 | 12/2012 | Fortier et al. | |
| 2013/0124523 A1* | 5/2013 | Rogers | G16H 10/60 |
| | | | 707/737 |
| 2013/0311472 A1* | 11/2013 | Cohen-Solal | G06F 16/285 |
| | | | 707/737 |
| 2014/0039924 A2 | 2/2014 | Barsoum et al. | |
| 2014/0129246 A1 | 5/2014 | Vdovjak et al. | |
| 2014/0350954 A1 | 11/2014 | Ellis et al. | |
| 2016/0019350 A1 | 1/2016 | Vdovjak et al. | |
| 2016/0203281 A1 | 7/2016 | Zalis et al. | |
| 2016/0304382 A1 | 10/2016 | Kim et al. | |
| 2017/0076046 A1* | 3/2017 | Barnes | G16H 40/20 |
| 2022/0122312 A1* | 4/2022 | Vega | G16H 30/40 |
| 2022/0165359 A1* | 5/2022 | Lee | G16H 10/20 |
| 2022/0165360 A1* | 5/2022 | Lee | G06F 16/2428 |

OTHER PUBLICATIONS

Colombet, I. et al., "Electronic implementation of guidelines in the EsPeR system: a knowledge specification method". International Journal of Medical Informatics (2005) 74, 597-604.
Banerjee, I et al., "Semantic annotation of 3D anatomical models to support diagnosis and follow-up analysis of musculoskeletal pathologies", International Journal of Computer Assisted Radiology and Surgery, Springer, DE, vol. 11, No. 5, Nov. 28, 2015, pp. 707-720.
FMA, http://sig.biostr.washington.edu/projects/fm/AboutFM.html.
Snomed, http://www.nlm.nih.gov/research/umls/Snomed/snomed_main.html.
http://www.obofoundry.org/.

* cited by examiner

EVALUATION OF DECISION TREE USING ONTOLOGY

CROSS-REFERENCE TO PRIOR APPLICATIONS

This application is the U.S. National Phase application under 35 U.S.C. § 317 of International Application No. PCT/EP2017/065810, filed on Jun. 27, 2017, which claims the benefit of European Patent Application No. 16176377.6, filed on Jun. 27, 2016. These applications are hereby incorporated by reference herein.

FIELD OF THE INVENTION

The invention relates to a system and a method for use in evaluating a clinical guideline. The invention further relates to a workstation or imaging apparatus comprising the system. The invention further relates to ontology data and guideline data for use with the system and method. The invention further relates to a computer readable medium comprising instructions arranged to cause a processor system to perform the method.

BACKGROUND OF THE INVENTION

Clinical guidelines, also referred to as clinical practice guidelines or medical guidelines, are designed to support decision-making processes in the clinical environment. The standard definition of such clinical guidelines is that of Field and Lohr, 1990: "systematically developed statements to assist practitioners and patient decisions about appropriate health care for specific circumstances". Various national and international clinical guidelines organizations exist for managing and making available clinical guidelines, including but not limited to the US National Guideline Clearinghouse in the United States and the German Guidelines Information Service in Germany. In addition, there may be clinical guidelines on a more local level, e.g., for use within a particular clinical site.

Although clinical guidelines have traditionally been paper-based and intended for evaluation by clinicians, Computer-Interpretable clinical Guidelines (CIGs) have been introduced. For example, the review-paper "*Computer-interpretable clinical guidelines: A methodological review*" by Mor Peleg et al., Journal of Biomedical Informatics, Vol. 46, Issue 4, August 2013, Pages 744-763, reviews the literature on CIGs-related methodologies since the inception of CIGs. In section 4.1.2, the publication "*Electronic implementation of guidelines in the EsPeR system: a knowledge specification method*" is cited which is said to provide a hierarchical decision tree comprising textual descriptions of possible decision conditions and corresponding elementary recommendations. Based on these textual descriptions, the variables of decision and their possible values are formulated.

Disadvantageously, such computer-interpretable clinical guidelines are still predominately evaluated manually by clinicians, as there currently exist no systems or methods which can reliably and fully automatically evaluate such guidelines.

WO 2015/198168 A1 discloses a system for visually rendering longitudinal patient data. The system makes use of a screen template defining at least one visual element for being rendered on a display, with an appearance of the visual element being defined by a visualization parameter.

US 2010/0094874 A1 discloses a method and an apparatus for retrieving additional information regarding a patient record such that clinical experts can be provided with the main specific background knowledge.

WO 2013/074971 A1 discloses systems and methods for graphical/based management and documentation of longitudinal care episodes.

SUMMARY OF THE INVENTION

It would be advantageous to obtain a system and method which may assist a user, such as a clinician or other health care professional, in evaluating a clinical guideline. In accordance with a first aspect of the invention, a system is provided for use in evaluating a clinical guideline, the system comprising:
  a guideline data interface configured to access guideline data defining a machine readable version of the clinical guideline in the form of a decision tree comprising at least one node and a decision rule associated with the node, wherein the decision rule comprises at least one variable representing a biomedical quantity;
  a patient data interface configured to access patient data;
  a processor configured to:
    extract the biomedical quantity from the patient data using an ontology which defines concepts and their relationships in a medical domain of the clinical guideline and which thereby relates the variable of the decision rule to the patient data;
    generate display data for display to the user, wherein the display data is indicative of the biomedical quantity and/or an outcome of an evaluation of the decision rule on the basis of the biomedical quantity;
    if the biomedical quantity cannot be extracted from the patient data using the ontology, generate the display data to present a view of the patient data to the user to enable the user to determine the biomedical quantity from the view.

In accordance with another aspect of the invention, a method is provided for use in evaluating a clinical guideline, the method comprising:
  accessing guideline data defining a machine readable version of the clinical guideline in the form of a decision tree comprising at least one node and a decision rule associated with the node, wherein the decision rule comprises at least one variable representing a biomedical quantity;
  accessing patient data;
  the method further comprising, using a processor:
    extracting the biomedical quantity from the patient data using an ontology which defines concepts and their relationships in a medical domain of the clinical guideline and which thereby relates the variable of the decision rule to the patient data;
    generating display data for display to the user, wherein the display data is indicative of the biomedical quantity and/or an outcome of an evaluation of the decision rule on the basis of the biomedical quantity; and
    if the biomedical quantity cannot be extracted from the patient data using the ontology, generating the display data to present a view of the patient data to the user to enable the user to determine the biomedical quantity from the view.

In accordance with another aspect of the invention, a computer readable medium is provided comprising transitory or non-transitory data representing instructions arranged to cause a processor system to perform the method.

The above aspects of the invention involve accessing guideline data defining a machine readable version of a clinical guideline. For example, the guideline data may be appropriately marked-up so that it may also be read by machines, or it may be intended principally for processing by machines. Specifically, the machine readable version of the clinical guideline may be constituted by a decision tree comprising one or more nodes and one or more decision rule(s) associated with respective ones of the one or more node(s). Typically, the decision tree may comprise a hierarchy of such nodes, with at least several of such nodes comprising decision rules. At least one of these decision rules comprises a variable representing a biomedical quantity. Effectively, the variable may represent a field in the decision rule to be 'filled in' by the biomedical quantity. The biomedical quantity may relate to a patient that may be subject of a current evaluation of the clinical guideline. A specific example is that the variable may represent an ejection fraction (EF), with the biomedical quantity being a value of the ejection fraction, e.g., percentage. As such, the biomedical quantity may represent a clinical finding, measurement, etc., relating to a patient.

Furthermore, patient data is accessed, relating to the patient that may be subject of a current evaluation of the clinical guideline. Such patient data may originate from various sources and be of various types. For example, the patient data may comprise or be constituted by an Electronic Health Record (EHR) of the patient, by patient exam data, etc.

In order to assist in the evaluation of one or more of the decision rules of the decision tree, the biomedical quantity which is evaluated in a decision rule is extracted from the patient data by a processor. For that purpose, use is made of an ontology which defines concepts and their relationships in a medical domain of the clinical guideline. Such ontologies are known per se in the clinical field. By selecting an ontology which relates to the medical domain of the clinical guidelines, the variable may be related to the patient data. For example, the ontology may indicate that the variable 'EF' may relate to a measurement of the ejection fraction in the patient data and thereby to a measured value of '32%'.

Data representing the biomedical quantity may be displayed to the user. Additionally or alternatively, the decision rule may be evaluated by the processor on the basis of the biomedical quantity, and an outcome of the evaluation of the decision rule may be displayed. For example, if the EF has been determined to be 32%, and the decision rule pertains to 'EF>30%?', the decision rule may be evaluated to be 'True'. For displaying the outcome, the processor generates display data, e.g., an output image, a string, etc.

The inventors have recognized that even when using an ontology, it may not always be possible to automatically extract the required biomedical quantity from the patient data. For example, it may not be possible for the processor to relate the variable to a biomedical quantity in the patient data. Another example is that the biomedical quantity may not be measured yet and may therefore not be explicitly comprised or readily extractable from the patient data. Rather than simply aborting or merely prompting the user to manually provide the biomedical quantity, the processor generates the display data to present a view of the patient data to the user to enable the user to determine the biomedical quantity from the view. Here, the term 'view' refers to a particular representation of the patient data, which may involve showing a specific part of the patient data, e.g., a particular examination report or image slice, and/or selecting a particular way of presenting the patient data. A specific example is that the view may be a multiplanar reformatting of a stack of 2D image slices of the patient which may be comprised in the patient data, e.g., as a result of an exam. For example, a diameter of a body site may not have been included in the patient data as a measurement value, but may be measured from a 2D image slice from the patient data.

Advantageously, the user is assisted in evaluating the clinical guideline even when it is not possible to automatically extract the biomedical quantity from the patient data. Namely, a specific view of the patient data is generated to enable the user to determine biomedical quantity from the view. It is thus avoided that the user has to manually determine which view is suitable for determining the biomedical quantity and request the view, e.g., using an image viewer application running on a workstation, or obtain the view in a different manner. Rather, such a view is automatically generated and presented to the user if the biomedical quantity cannot be readily extracted from the patient data.

Optionally, the processor is configured to determine the view of the patient data on the basis of the ontology being indicative of a relationship between the variable and the view of the patient data. The ontology may be indicative of a relationship between the variable and the view of the patient data, as it relates concepts in the medical domain to each other. For example, if the variable relates to 'LAD stenosis', the ontology may relate this to an anatomical structure, namely the left anterior descending coronary artery (LAD). As such, if there exists image data of the left anterior descending coronary artery, a view of said image data may be provided. Another example is that textual patient data relevant to the (functioning of the) left anterior descending coronary artery may be presented to the user to enable the user to determine the biomedical quantity, e.g., the degree of stenosis of the LAD.

Additionally or alternatively, the ontology may be purposefully generated to comprise definitions of standard views in relation to (measurable) variables. For example, a node may be defined in the ontology which indicates that the stenosis of the LAD may be observed by coronary angiography. A specific example may be that the ontology comprises a parametrization of the views, e.g., one or more view parameters, such as 'LAO 50 Cranial 30' denoting 50 degree of LAO rotation and 30 degrees cranial projection.

Optionally, the ontology comprises the relationship between the variable and the view in the form of an 'is-visible-in' object representing a link between concepts in the ontology. For example, the ontology may link 'BodySite-Cornaries-LAD' by an 'is-visible-in' or similar object to 'Angiographic Standard view LAO 50 Cranial 30'.

Optionally, the view is of a medical image or geometric model comprised in the patient data. If the biomedical quantity cannot be extracted from the patient data, a specific view of a medical image or geometric model may be presented to the user. For example, if the medical image is a volumetric image, a projection with a particular type of geometry, field of view and/or camera pose may be generated, e.g., using known volume projection techniques. Similarly, the geometric model, which may be patient-specific in that it may have been fitted to image data of the patient, may be rendered with a particular type of geometry, field of view and/or camera pose. Here, the term 'geometric model' may refer to a model for segmentation, e.g., a deformable surface model, which may represent a geometry of an anatomical structure, e.g., in the form of a multi-compartmental mesh of triangles.

It will be appreciated that the geometrical model may allow generating views which are more informative for determining the biomedical quantity than views generated from the patient data. For example, a medical image may insufficiently show an anatomical structure, e.g., as it may be occluded by another anatomical structure. After fitting the geometric model to the medical image, the location of various anatomical structures in the image data is known which in turn allows to generate informative views. For example, a view may be generated where the aortic valve fully visible, which may normally be occluded in a medical image. The parts of the geometrical model may be semantically labeled, allowing the geometric model to be linked to the ontology, e.g., to body sites referred by the ontology.

Optionally, the ontology comprises one or more view parameters which define the view, and the processor is configured to generate the view based on the one or more view parameters. Optionally, the one or more view parameters comprise at least one of: a field of view parameter, and a camera pose parameter. Such view parameters are examples of a 'configuration' of the view which specifies how the view is to be generated.

Optionally, the patient data comprises the medical image and the geometric model, and the processor is configured to select between presenting the view of the medical image and presenting the view of the geometric model on the basis of a visibility criterion which is indicative of how well each view is suitable for enabling the user to determine the biomedical quantity. If both image data and a geometric model are available which may in principle enable the user to determine the biomedical quantity, the processor may select between both on the basis of a visibility criterion which is indicative of how well each view is suitable for enabling the user to determine the biomedical quantity. Accordingly, the user may be provided with the more informative view of both views. The visibility criterion may be predefined for a particular body site, clinical finding, etc. In particular, the ontology may define so-termed 'standard views' for body sites, clinical finding, etc., with the adjective 'standard' referring to the view being considered a reference in the clinical profession and/or by the clinical guideline itself. The absence of a definition of a standard view in the ontology in relation to a particular body site, clinical finding, etc., may serve as visibility criterion in that it may indicate to the processor that no suitable standard view exists or has been defined and that therefore the view should be generated from the geometric model.

Optionally, the system further comprises a user interface subsystem configured to enable the user to perform a measurement with respect to the view to determine the biomedical quantity. Determining the biomedical quantity may involve performing a measurement, e.g., on a medical image or geometric model. It is thus not needed for the user to perform the measurement mentally, as the user may rather use the user interface.

Optionally, the processor is configured to extract the biomedical quantity from the patient data using a reasoning engine. Reasoning engines are also known as inference engines, and may be used to extract the biomedical quantity from the patient data by applying logical rules, such as IF-THEN rules, to the patient data and the ontology.

In a further aspect of the invention, a computer readable medium may be provided comprising transitory or non-transitory ontology data defining a machine readable version of an ontology which defines concepts and their relationships in a medical domain of a clinical guideline, wherein the ontology comprises one or more view parameters which define a view of a medical image or geometric model. For example, the ontology may comprise the view parameters in relationship with medical concepts such as body sites or clinical findings. Examples of such view parameters include but are not limited to a geometry, field of view and camera pose.

In a further aspect of the invention, computer readable medium may be provided comprising transitory or non-transitory guideline data defining a machine readable version of a clinical guideline in the form of a decision tree comprising at least one node and a decision rule associated with the node, wherein the decision rule comprises at least one variable representing a biomedical quantity, and wherein the variable is identified in the guideline data in accordance with an ontology which defines concepts and their relationships in a medical domain of the clinical guideline It will be appreciated by those skilled in the art that two or more of the above-mentioned embodiments, implementations, and/or optional aspects of the invention may be combined in any way deemed useful.

Modifications and variations of the method and/or the computer readable media, which correspond to the described modifications and variations of the system, can be carried out by a person skilled in the art on the basis of the present description.

A person skilled in the art will appreciate that the system and method may be applied to multi-dimensional image data, e.g., two-dimensional (2D), three-dimensional (3D) or four-dimensional (4D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

BRIEF DESCRIPTION OF THE DRAWINGS

These and other aspects of the invention will be apparent from and elucidated further with reference to the embodiments described by way of example in the following description and with reference to the accompanying drawings, in which.

It should be noted that the figures are purely diagrammatic and not drawn to scale. In the figures, elements which correspond to elements already described may have the same reference numerals.

LIST OF REFERENCE NUMBERS

Figure 1:
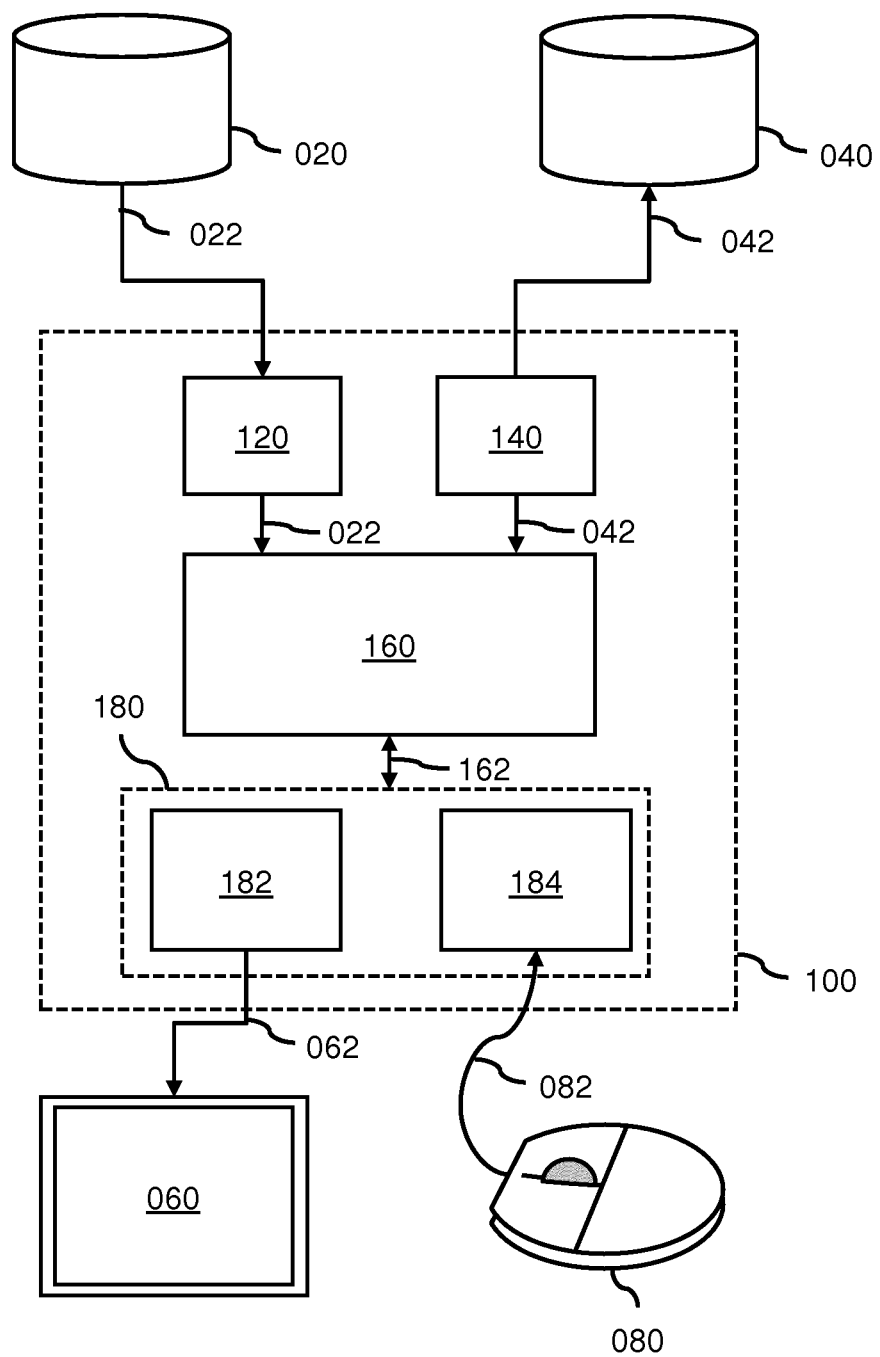
FIG. 1 shows a system for use in evaluating a clinical guideline.

The following list of reference numbers is provided for facilitating the interpretation of the drawings and shall not be construed as limiting the claims.
020 guideline database
022 guideline data
040 patient database
042 patient data
060 display
062 display data
080 user input device
082 user input data
100 system for use in evaluating clinical guideline
120 guideline data interface
140 patient data interface
160 processor
162 data communication
180 user interface subsystem
182 display output interface
184 user input interface
200, 202 decision tree
210-216 node comprising decision rule
220, 222 traversing of nodes
240 extract from ontology
300 reasoning engine
310 patient data
320 ontology data
330 clinical question
340 answer inferred from patient data
350 view parameters inferred from ontology
400 view of medical image
410 view of geometric model
500 method for use in evaluating clinical guideline
510 extract biomedical quantity
520 biomedical quantity extractable?
530 display extracted biomedical quantity
540 identify view
550 display view
600 computer readable medium
610 non-transitory data representing instructions

DETAILED DESCRIPTION OF EMBODIMENTS

FIG. 1 shows a system 100 for use in evaluating a clinical guideline. The system 100 is shown to comprise a guideline data interface 120 configured to access guideline data 022 defining a machine readable version of the clinical guideline. In particular, the guideline data 022 may define a machine readable clinical guideline in the form of a decision tree comprising at least one node and a decision rule associated with the node, with the decision rule comprising at least one variable representing a biomedical quantity.

The system 100 is further shown to comprise a patient data interface 140 configured to access patient data 042. A non-limiting example of such patient data 042 is data representing an Electronic Health Record (EHR) of the patient, patient exam data, etc. As explained with reference to FIGS. 6 and 7, the patient data 042 may also comprise one or more medical images, e.g., as acquired during patients exams, and/or one or more geometric models which may be fitted to anatomical structures in the medical images.

In the example of FIG. 1, each of the interfaces 120, 140 is shown to be connected to a respective external database which is shown to comprise the accessed data, namely a guideline database 020 comprising the guideline data 022 and a patient database 040 comprising the patient data 042.

In a specific example, each of the databases 020, 040 may be part of a Hospital Information System (HIS). However, this is not a limitation, in that the databases 020, 040 may also be separately provided, or in that the guideline data 022 and/or the patient data 042 may be accessed from another data storage. In general, each of the interfaces 120, 140 may take various forms, such as a network interface to a local or wide area network, e.g., the Internet, a storage interface to an internal or external data storage, etc.

The system 100 is further shown to comprise a processor 160, such as a computer processor or microprocessor, which may be configured, e.g., by appropriate software, to perform the following operations during operation of the system:
extract the biomedical quantity from the patient data using an ontology which defines concepts and their relationships in a medical domain of the clinical guideline and which thereby relates the variable of the decision rule to the patient data;
generate display data for display to the user, wherein the display data is indicative of the biomedical quantity and/or an outcome of an evaluation of the decision rule on the basis of the biomedical quantity; and
if the biomedical quantity cannot be extracted from the patient data using the ontology, generate the display data to present a view of the patient data to the user to enable the user to determine the biomedical quantity from the view.

These operations of the system 100, including various optional aspects thereof, will be further described with reference to FIGS. 2-7.

FIG. 1 further shows an optional aspect of the system 100, in that the system 100 may comprise a user interface subsystem 180 which comprises, or is constituted by, a display output interface 182 and a user input interface 184. The display output interface 182 may be configured for outputting the display data 062 generated by the processor 160 to an external display 060. The user input interface 184 may be configured to receive user input commands 042 from a user input device 040 to enable a user to interact with the system, e.g., to operate a graphical user interface, to perform measurements onscreen, etc. The user input device 080 may take various forms, including but not limited to a computer mouse, touch screen, keyboard, etc. FIG. 1 shows the user input device to be a computer mouse 080. In general, the user input interface 184 may be of a type which corresponds to the type of user input device 080, i.e., it may be a thereto corresponding user device interface.

In general, the system 100 may be embodied as, or in, a single device or apparatus, such as a workstation. The device or apparatus may comprise one or more computer processors or microprocessors which execute appropriate software. The software may have been downloaded and/or stored in a corresponding memory, e.g., a volatile memory such as RAM or a non-volatile memory such as Flash. Alternatively, the interfaces and processor may be implemented in the device or apparatus in the form of programmable logic, e.g., as a Field-Programmable Gate Array (FPGA). In general, the interfaces and the processor may be implemented in the form of a circuit. The system 100 may also be implemented in a distributed manner, e.g., involving different devices or apparatuses.

As further context to the operation of the system 100 of FIG. 1, it is noted that when performing diagnosis or classification, a clinician may be faced with a large amount of complex imagery and other heterogeneous medical data. Since there are no unified and patient-specific representations of medical data, the clinician typically has to integrate data from multiple sources. As such, it may be difficult for the clinician to obtain an adequate overview of the patient's medical record in order to make reliable decisions. In recent years, clinical guidelines have become a popular tool to increase the accuracy and decrease the time for carrying out diagnosis and classification. However, clinical guidelines only partially standardize the workflow. The quality of a diagnosis still significantly depends on the skill of the clinician since such clinical guidelines are typically evaluated manually. A reason for this is that, for a given question in the clinical guideline, the interpretation of the question on the one hand, and the way of how to gather the medical information that is required to answer the question on the other hand, may predominately depend on the skill of the particular clinician.

Recently, there has been significant effort to come up with a unified representation of the patient's anatomy as well as her/his record of medical events such as diagnosis, therapies or interventions. This representation is typically mostly based on a personalized ontology that is a subset of de-facto standards such as FMA (Foundational Model of Anatomy, http://sig.biostr.washington.edu/projects/fm/ AboutFM.html) or SNOMED CT (Systematized Nomenclature of Medicine-Clinical Terms, http://www.nlm.nih.gov/ research/umls/Snomed/snomed_main.html)]. These ontologies formally define concepts and their relationships in a medical domain.

The system of FIG. 1 may make use of such an ontology to perform reasoning or to query information from patient data. In particular, the ontology may be used to relate variables of decision rules to the patient data. For that purpose, the variables of the decision rules may be explicitly linked to concepts in the ontology, thereby allowing the system to identify patient data which is related to a variable on the basis of the patient data linking to a same or related concept in the ontology. Additionally, these ontologies may be linked to geometrical models. State of the art software tools that are part of Philips diagnostic solutions already allow to easily fit (annotated) geometric models to various data such as MRI, CT or ultrasound. Once a link between such models and the ontology is established, geometric relationships may also be incorporated to perform reasoning or to query information.

Figure 2:
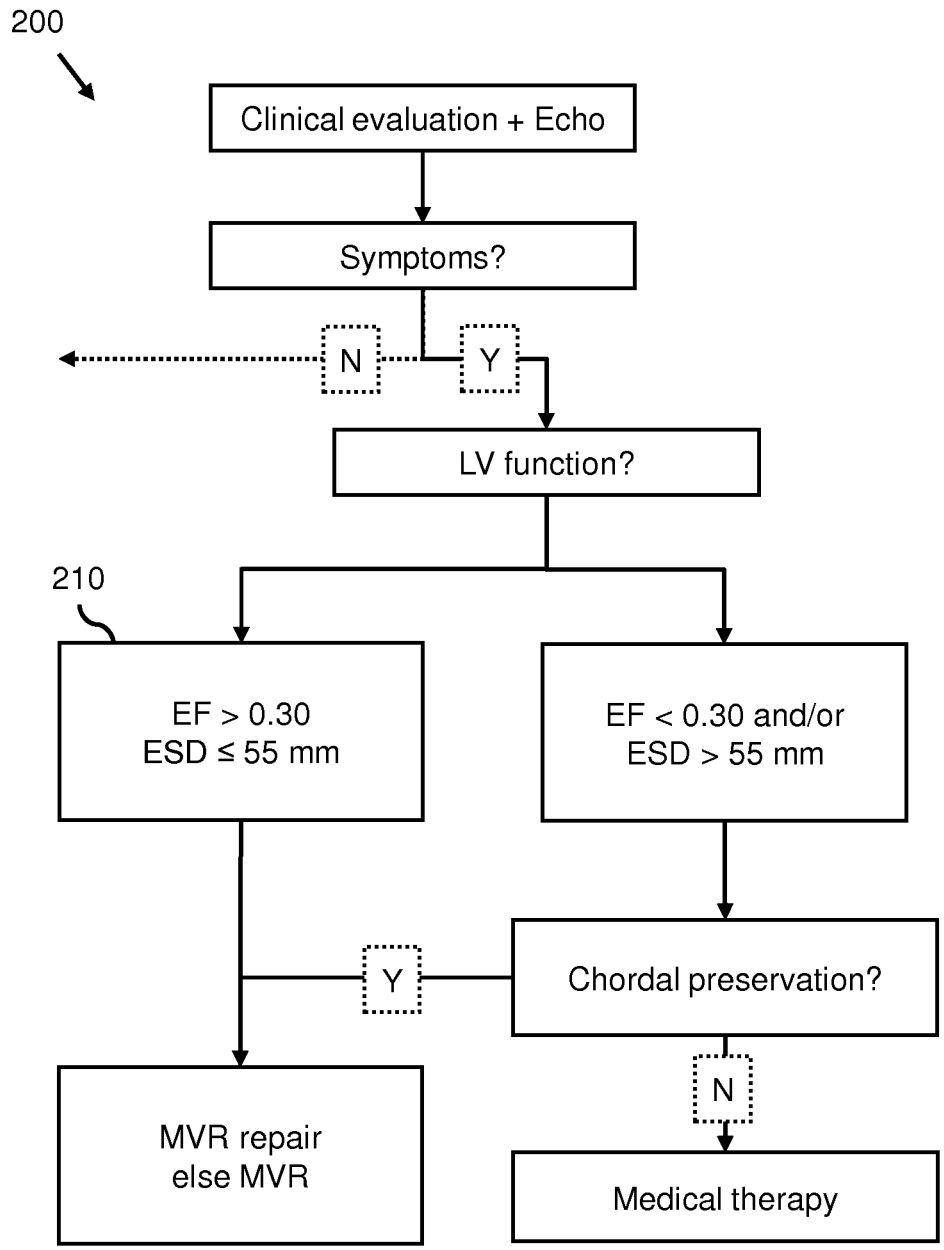
FIG. 2 shows a machine readable version of the clinical guideline in the form of a decision tree comprising nodes and decision rules associated with the nodes.

FIG. 2 shows an example of a machine readable version of (part of) a clinical guideline, e.g., relating to Chronic Severe Mitral Regurgitation, in the form of a decision tree 200 comprising nodes 210 and decision rules associated with the nodes. As indicated before, such decision trees may be simple but powerful tools to standardize diagnosis and classification tasks within the medical domain. The decision tree may comprise nodes, where each node is associated with a question. A clinician may manually traverse the decision tree by answering the question that is associated to the respective node. Depending on the answer, the clinician may proceed to one of the child nodes until the end of the decision tree is reached, at which point the decision tree may provide a diagnosis, classification or define another type of outcome. It is noted that the questions associated with the nodes may be given both as human-readable sentences and as structured data. The format of this data may be optimized such that it can be processed by the system, e.g., by being based on predicate logic. For example, the following table provides examples of the question in human-readable form (first column), the predicate logic representing the question in machine-readable form (second column) and possible answers to the question (third column).

| Question | Predicate Logic | Possible Answers |
|---|---|---|
| Is the ejection fraction (EF) above 30%? | EF > 30% ? | Yes/No |
| Does the patient have a left-dominant coronary circulation (CC)? | CC == left-dominant? | Yes/No |

Figure 3:
FIG. 3 shows an extract from an ontology which defines concepts and their relationships in a medical domain of the clinical guideline.

FIG. 3 shows an extract 240 from a SNOMED CT ontology, which is provided for illustration purposes only, namely to illustrate that an ontology may comprise concepts, such as body sites, anatomical objects and structures, and relationships between concepts. In the specific example of FIG. 3, it can be seen that the ontology comprises the concept 'Atrioventicular node branch of right coronary artery' and the relationship between this concept and another concept, e.g., 'Entire heart', in the form of a 'Part of' object representing a link between the concepts in the ontology. As such, the ontology defines that the atrioventicular node branch of right coronary artery is part of the entire heart. It is noted that the ontology may be represented in machine-readable form as a tree-like structure comprising nodes representing concepts and edges representing relations between the concepts. In such a representation, the 'Part of' object may be represent as an edge.

Figure 4:
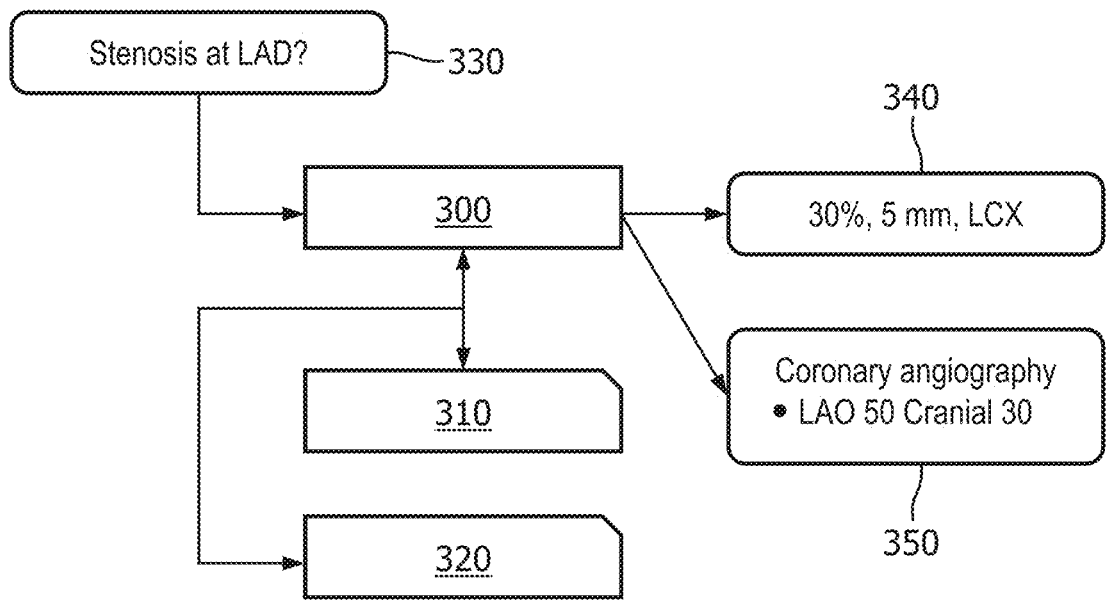
FIG. 4 illustrates an evaluation of a decision rule by the system of FIG. 1.

FIG. 4 illustrates the evaluation of a decision rule by the system of FIG. 1, with the decision rule representing a question from a clinical guideline. It will be appreciated that although the decision rule 330 is shown in the form of the human-readable question 'Stenosis at LAD?', it may be differently represented in machine-readable form. For example, the decision rule 330 may formulated as a Boolean expressions following first order predicate logic. Typically, the evaluation of the decision rule 330 may pertain to a) extracting a biomedical quantity from patient data, such as a scalar, and b) processing the extracted biomedical quantity by first order predicates such as 'equal', 'less', 'is part of', etc. To evaluate the decision rule, and thereby answer the question of the clinical guideline, a reasoning engine 300 may be used which may access an ontology 320 in the current medical domain as well as patient data 310 of the patient. If the question requires information that is already available or that can be directly inferred from the patient data 310, the reasoning engine 300 may extract that information automatically and evaluate the respective node of the decision tree. In particular, if the information concerns a biomedical quantity which has already been measured and is available as a finding/observation or measurement in the patient data 310, the information may be extracted directly. The information may also be directly extracted by the reasoning engine 300 if it concerns general information such as age or gender, or information about the patient's anatomy, e.g., coronary anomalies.

It will be appreciated that instead of a reasoning engine, another type of inference technique may be employed by the system, as known per se within the field of artificial intelligence. Moreover, the reasoning engine or other technique may be available to the system in the form of software, e.g., a list of instructions for the processor of the system, which when executed by the processor perform the operations of the reasoning engine.

Having extracted the information, the extracted information may be presented to the user for validation before being used by the system. For example, the system may display the extracted information and may only proceed with evaluating the respective node on the basis of the extracted information once the user confirms the validity of the extracted information. Additionally or alternatively, the inferred answer may be presented to the user for validation before being used by the system. As such, the system may display the inferred answer and may only proceed with evaluating a following clinical question once the user confirms the validity of the inferred answer. For these purposes, the user may make use of a user input device which may be connected to a user interface subsystem of the system.

In the example of FIG. 4, the system may be able to infer an answer 340 from the patient data 310 in the form of '30%, 5 mm, LCX' to 'Stenosis at LAD?'.

If the reasoning engine 300 is not able to infer a unique answer, the user may be presented with a set of possible solutions sorted by their confidence. Additionally or alternatively, the system may propose a suitable standard view that allows the clinician to extract the information manually, e.g., by deriving a set of view parameters 350 from the ontology 320. This aspect will be further explained with reference to FIGS. 6 and 7.

Figure 5:
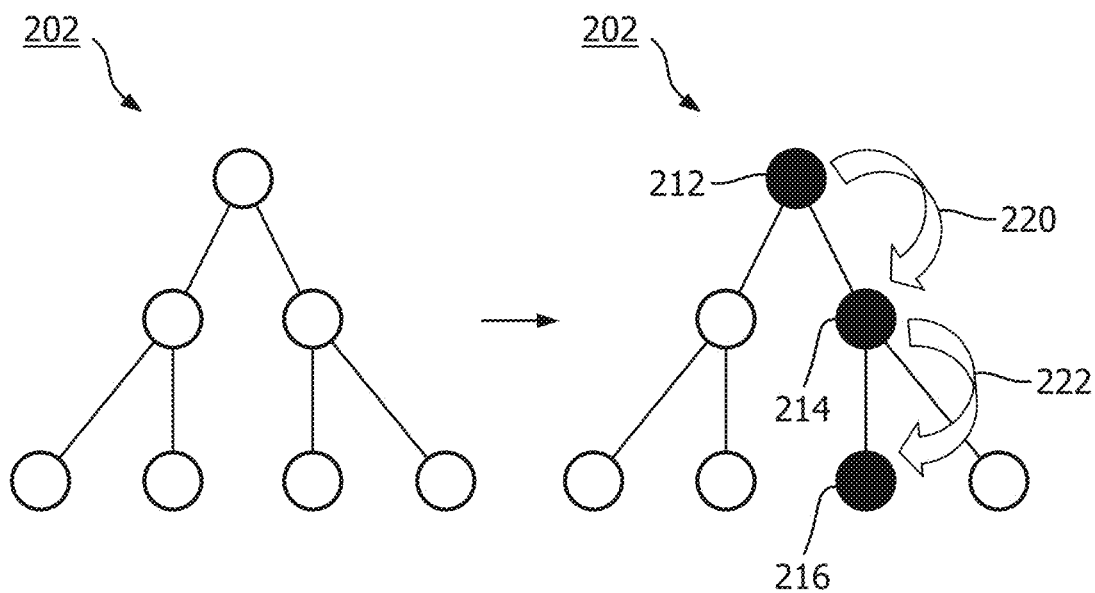
FIG. 5 illustrates an evaluation of a decision tree by the system of FIG. 1.

FIG. 5 illustrates an evaluation of a decision tree 202 by the system of FIG. 1 in which the system traverses through the decision tree's nodes. In this example, the system may evaluate the decision rule of parent node 212, and after determining an answer to the question represented by the decision rule, traverse from the parent node 212 to a child node 214 in a first traverse step 220. The system may then evaluate the decision rule of the child node 214, and after determining the answer, traverse from the child node 214 to another child node 216 in a second traverse step 222. The selection of child nodes 214, 216 may be at each step dependent on the answer to the current decision rule. It will be appreciated that although the system may autonomously transverse through the decision tree 202, the user may be involved as well, e.g., to confirm the validity of the extracted information and/or of the inferred answer. Such user involvement may also be dependent on the confidence the system, and in particular the reasoning engine, has in the correctness of the answer. The confidence may be a parameter estimated by the reasoning engine using known techniques. As such, the user may only be prompted to confirm the validity of the extracted information and/or the inferred answer if the confidence in the answer is relatively low, e.g., below a threshold.

Figure 6:
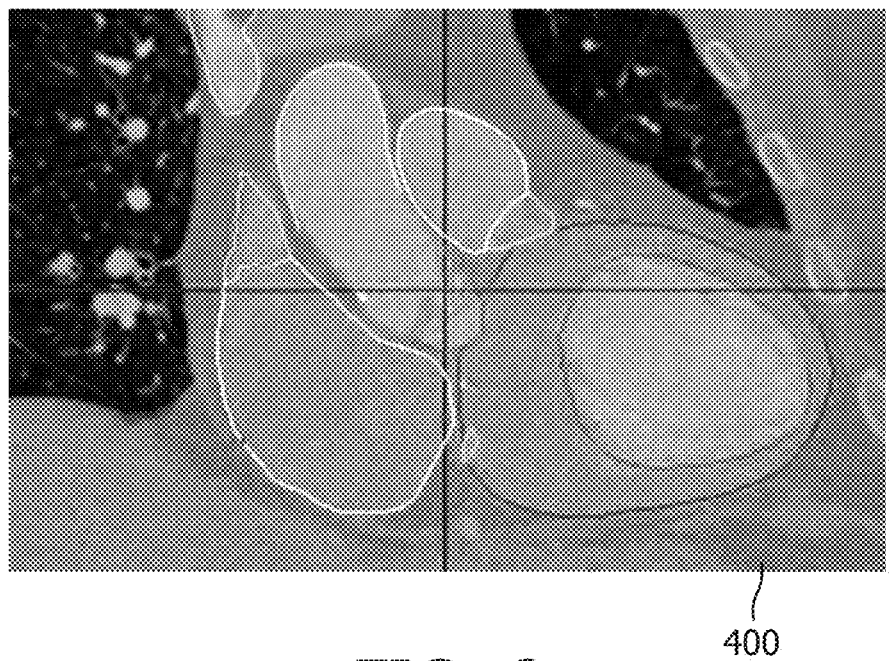
FIG. 6 shows a view of a medical image, which may be generated by the system of FIG. 1 to enable a user to determine a biomedical quantity.
Figure 7:
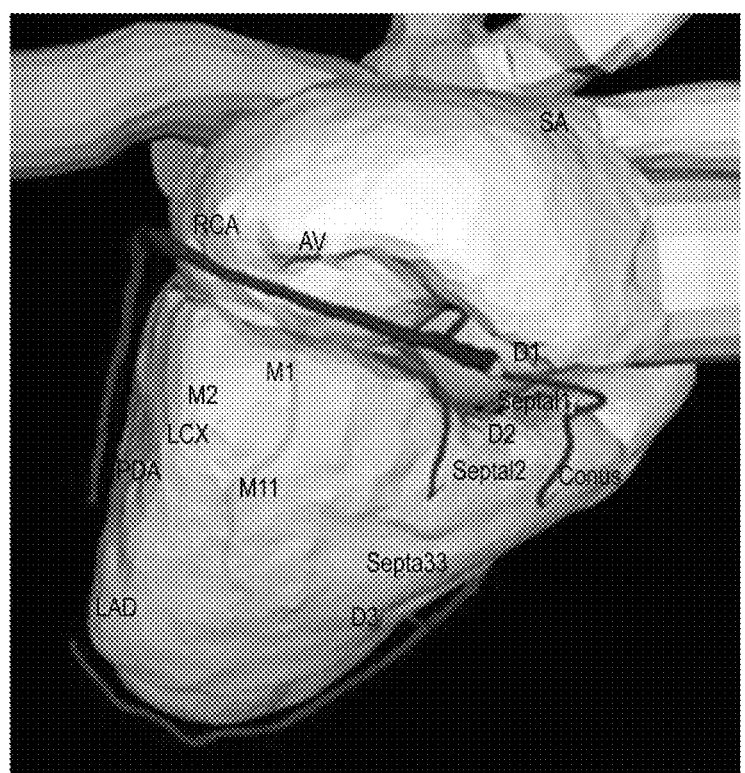
FIG. 7 shows a view of a geometric model, which may be generated by the system of FIG. 1 additionally or alternatively to the view of the medical image.

FIG. 6 shows a view of a medical image 400 and FIG. 7 shows a view of a geometric model 410, both of which may be generated by the system of FIG. 1 to enable a user to manually determine a biomedical quantity. Similar to the direct inference of an answer using the ontology, e.g., as previously described with reference to FIG. 4, the configuration of the view may be determined using the ontology. For example, the ontology may be indicative of a relationship between the variable of the decision rule and the view. Namely, body sites as well as findings may be linked to views by a relationship such as 'is visible in', which may be embodied as an object representing a link between concepts in the ontology. As such, for a given variable to be extracted, the ontology may be traversed in order to find all possible pathways to a standard view. It is noted that the ontology may be structured as a tree comprising nodes and edges. An example of an 'is-visible-in' relationship, which may represent an edge in such a tree, is the following, denoting that ejection fraction measurements are visible in an echocardiography-long axis view:

Measurements-EF>is visible in>echocardiography-long axis view

In general, the view may be inferred from the ontology by traversing along 'is-visible-in' edges in the ontology's tree until an indication of a view is encountered.

In another example, a body site may be identified from which the view may be parametrized. For example, if the question relates to coronary stenosis, it may be determined from the ontology that coronary stenosis is typically observed in angiographic images. Moreover, the ontology may link that concept to a body site which allows to infer the orientation (e.g., 'LAO 50 Cranial 30'), as shown in the following sequence in the ontology:

Findings-Coronary Stenosis>is visible in>Angio graphic View

Findings-Coronary Stenosis>located-in>BodySite-Cornaries-LAD

BodySite-Cornaries-LAD>is-visible-in>Angiographic Standard view

LAO 50 Cranial 30

In general, a type of view such as coronary angiography, CT slice view, or 3D model, and a corresponding configuration may be inferred from the ontology.

Moreover, in general, medical visualizations may be represented as concepts within medical ontologies such as SNOMED. The following examples are extracts from an ontology which define a standard visualization with attributes and relations to other nodes in the ontology. A view has (geometric) parameters such as field of view or camera pose. Furthermore it references body sites that are commonly visualized by the given type.

Coronary Sketch

Body Sites
Coronary Arteries
Parameters
Angulation
Field of View
Standard Configurations
LAO 50 Cranial 30
RAO 45 Caudal 40
Observations
Stenosis
Another example:

3D View IsoSurface

Body Sites
Entire Body
Parameters
Camera Pose
IsoValue
Standard Configurations
Head Frontal
Face Perspective
Observations
Tumor In the following examples, clinical findings, body sites or measurements are linked to standard views.

Stenosis of Coronary Artery

Body Site
Coronary Arteries
Standard Visualizations
Coronary Angiography
Coronary Sketch LAD
  Parent
    Left Coronary Artery Tree
    Entire Coronary Artery Tree
  Standard Visualizations
    Coronary Angiography, LAO 50 Cranial 30
    Coronary Sketch, Left Dominant The ontology may be specifically generated to comprise such standard visualizations, e.g., in the form of view parameters, in relation to concepts such as body sites, findings, etc. In addition, the decision tree may be generated to reference the concepts in the ontology. Thereby, the inference of the views from the ontology may be facilitated.

In general, given a biomedical quantity that needs to be measured, the system may determine the most suitable visualization (view), as well as its configuration based on cross-referencing within the ontology, e.g., by linking the biomedical quantity to the ontology and traversing the ontology to determine the view. Two cases may be considered:

Standard configuration: if the biomedical quantity can be observed or measured by one of the pre-defined standard configurations in the ontology, the standard configuration may be directly used. For example, the ontology may define that a stenosis of the LAD can be observed by coronary angiography (parametrization: LAO 50 Cranial 30).

Free configuration: for many types of views, standard configurations are not always clearly defined within the ontology. However, if an annotated, patient-registered geometric model is available, the configuration of the view may be inferred geometrically. Namely, parts of the model may be linked to the corresponding concepts in the ontology. As such, a camera pose or field of view of the geometric model may be computed that clearly shows the region of interest. For example, in the coronary tree example, the viewpoint may be configured such that the foreshortening of the investigated segment is minimized.

Figure 8:
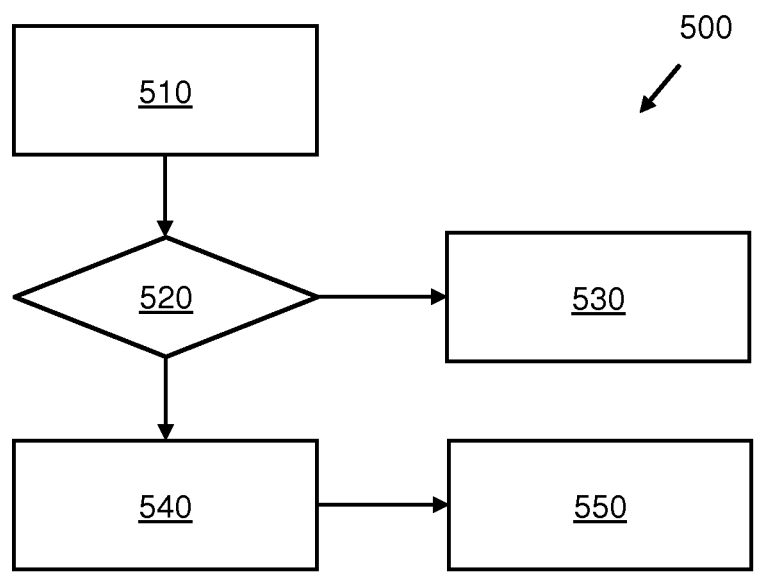
FIG. 8 shows a method for use in evaluating a clinical guideline.

FIG. 8 shows a method 500 for use in evaluating a clinical guideline. The method 500 may correspond to an operation of the system of FIG. 1, although this is not a limitation. Moreover, although explicitly not shown in FIG. 8, the method 500 may comprise accessing guideline data and patient data as described with reference to the system.

The method 500 may comprise, in an operation titled "EXTRACT BIOMEDICAL QUANTITY", extracting 510 the biomedical quantity from the patient data using an ontology as described with reference to the system. The method 500 may further comprise, in an operation titled "BIOMEDICAL QUANITY EXTRACTABLE?" determining 520 whether the biomedical quantity could be extracted. If so, the method 500 may comprise, in an operation titled "DISPLAY EXTRACTED BIOMEDICAL QUANTITY", generating 530 display data for display to the user, wherein the display data is indicative of the biomedical quantity and/or an outcome of an evaluation of the decision rule on the basis of the biomedical quantity. If the biomedical quantity cannot be extracted from the patient data using the ontology, the method 500 may comprise, in an operation titled "IDENTIFY VIEW", identifying 540 a view of the patient data to enable the user to determine the biomedical quantity from the view, and in a operation titled "DISPLAY VIEW", generating and displaying 550 display data to present the view to the user.

Figure 9:
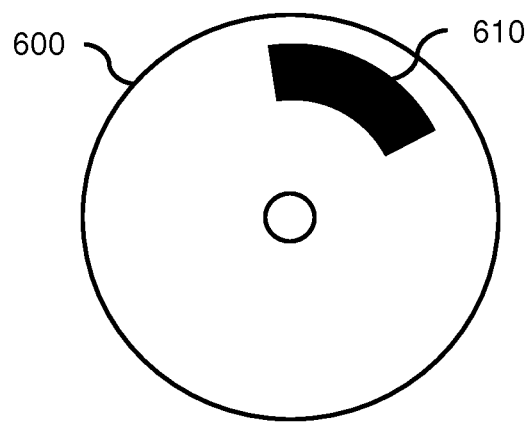
FIG. 9 shows a computer readable medium comprising instructions for causing a processor system to perform the method.

The method may be implemented on a computer as a computer implemented method, as dedicated hardware, or as a combination of both. As also illustrated in FIG. 9, instructions for the computer, e.g., executable code, may be stored on a computer readable medium 600, e.g., in the form of a series 610 of machine readable physical marks and/or as a series of elements having different electrical, e.g., magnetic, or optical properties or values. The executable code may be stored in a transitory or non-transitory manner. Examples of computer readable mediums include memory devices, optical storage devices, integrated circuits, servers, online software, etc. FIG. 9 shows an optical disc 600. Additionally or alternatively, the computer readable medium 600 may comprise transitory or non-transitory ontology data 610 defining a machine readable version of an ontology. Additionally or alternatively, the computer readable medium 600 may comprise transitory or non-transitory guideline data 610 defining a machine readable version of a clinical guideline.

It will be appreciated that the described system and method may be used in an interactive reasoning framework that is used for diagnosis and classification. Likewise, the system and method may be used for planning applications, where not findings but procedures are queried in order to get an optimal visualization or perspective of pre-operative data such as CT or MRI volumes. Various other applications are conceived as well.

Examples, embodiments or optional features, whether indicated as non-limiting or not, are not to be understood as limiting the invention as claimed.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be subdivided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk.

Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for use in evaluating a clinical guideline, the system comprising:
   a guideline data interface configured to access guideline data defining a non-transitory machine readable version of the clinical guideline in the form of a decision tree encoded in at least one Boolean expression providing a standardized patient diagnosis comprising at least one node and a decision rule associated with the node, wherein the decision rule comprises at least one variable representing a biomedical quantity;
   a patient data interface configured to access patient data stored on an electronic health record;
   a processor configured to:
      extract the biomedical quantity from the patient data stored on the electronic health record using an ontology which defines concepts and their relationships in a medical domain of the clinical guideline data and which thereby relates the variable to the decision rule to the patient data, wherein the ontology comprises one or more view parameters including one or more of a camera pose or a field of view, wherein the processor is configured to generate a view based on the one or more view parameters;
      generate display data for display to the user, wherein the display data is indicative of one or more of the biomedical quantity or an outcome of an evaluation of the decision rule on the basis of the biomedical quantity; and
      if the biomedical quantity cannot be extracted from the patient data using the ontology, automatically generate the display data to present a view of the patient data to the user to enable the user to determine the biomedical quantity from the view, wherein the view comprises a geometric model included in the patient data, wherein the geometric model is rendered with a geometry specific to the patient, the view computed to show a region containing the biomedical quantity and based on the ontology.

2. The system according to claim 1, wherein the system further comprises a user interface subsystem configured to enable the user to perform a measurement with respect to the view to determine the biomedical quantity.

3. The system according to claim 1, wherein the processor is configured to extract the biomedical quantity from the patient data.

4. The system according to claim 3, wherein the processor is configured to identify a set of biomedical quantities which each represent the biomedical quantity to be extracted, and generate the display data to be indicative of the set of biomedical quantities sorted by their confidence.

5. A computer-implemented method for use in evaluating a clinical guideline, the method comprising:
   accessing guideline data comprising a decision tree encoded in at least one Boolean expression providing a standardized patient diagnosis comprising at least one node and a decision rule associated with the node, wherein the decision rule comprises at least one variable representing a biomedical quantity;
   accessing patient data;
   extracting the biomedical quantity from the patient data using an ontology which defines concepts and their relationships in a medical domain of the clinical guideline data and which thereby relates the variable of the decision rule to the patient data, wherein the ontology comprises one or more view parameters;
   generating a view based on the one or more view parameters;
   generating display data for display to the user, wherein the display data is indicative of one or more of the biomedical quantity or an outcome of an evaluation of the decision rule on the basis of the biomedical quantity; and
   if the biomedical quantity cannot be extracted from the patient data using the ontology, automatically generating the display data to present a view of the patient data to the user to enable the user to determine the biomedical quantity from the view, wherein the view comprises a geometric model included in the patient data, wherein the geometric model is rendered with a geometry specific to the patient, the view computed to show a region containing the biomedical quantity and based on the ontology.

6. A non-transitory computer readable medium storing instructions that, when executed by one or more processors, cause the one or more processors to:
   access guideline data comprising a decision tree encoded in at least one Boolean expression providing a standardized patient diagnosis comprising at least one node and a decision rule associated with the node, wherein the decision rule comprises at least one variable representing a biomedical quantity;
   access patient data;
   extract the biomedical quantity from the patient data using an ontology which defines concepts and their relationships in a medical domain of the clinical guideline data and which thereby relates the variable of the decision rule to the patient data, wherein the ontology comprises one or more view parameters;
   generate a view based on the one or more view parameters;
   generate display data for display to the user, wherein the display data is indicative of one or more of the biomedical quantity or an outcome of an evaluation of the decision rule on the basis of the biomedical quantity; and if the biomedical quantity cannot be extracted from the patient data using the ontology, automatically generate the display data to present a view of the patient data to the user to enable the user to determine the biomedical quantity from the view, wherein the view comprises a geometric model included in the patient data, wherein the geometric model is rendered with a geometry specific to the patient, the view computed to show a region containing the biomedical quantity and based on the ontology.

7. The method of claim 5, wherein the patient data further comprises a stack of 2D image slices of the patient.

8. The method of claim 5, wherein the view further comprises a multiplanar reformatting of a stack of image slices of the patient.

9. The method of claim 5, wherein the geometric model is further rendered with a predetermined field of view.

10. The non-transitory computer readable medium of claim 6, wherein the patient data further comprises a stack of 2D image slices of the patient.

11. The non-transitory computer readable medium of claim 6, wherein the view further comprises a multiplanar reformatting of a stack of images slices of the patient.

12. The non-transitory computer readable medium of claim 6, wherein the geometric model is further rendered with a predetermined field of view.

* * * * *